(12) United States Patent
Malinowski

(10) Patent No.: US 7,479,146 B2
(45) Date of Patent: Jan. 20, 2009

(54) CRANIAL BURR HOLE PLUG AND INSERTION TOOL

(75) Inventor: Zdzislaw B Malinowski, Castaic, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1078 days.

(21) Appl. No.: 10/635,092

(22) Filed: Aug. 6, 2003

(65) Prior Publication Data

US 2004/0034367 A1 Feb. 19, 2004

Related U.S. Application Data

(60) Provisional application No. 60/403,787, filed on Aug. 14, 2002.

(51) Int. Cl.
*A61B 19/00* (2006.01)

(52) U.S. Cl. ..................................................... 606/130

(58) Field of Classification Search ................. 606/130, 606/129; 607/116, 139, 149; 600/377, 378, 600/386; 604/175
See application file for complete search history.

(56) References Cited

U.S. PATENT DOCUMENTS

| | | | |
|---|---|---|---|
| 4,245,645 A | 1/1981 | Arseneault et al. | |
| 4,328,813 A | 5/1982 | Ray | |
| 4,826,487 A | 5/1989 | Winter | |
| 4,850,359 A | 7/1989 | Putz | |
| 4,931,056 A | 6/1990 | Ghajar et al. | |
| 4,955,891 A * | 9/1990 | Carol | 606/130 |
| 4,998,938 A | 3/1991 | Ghajar et al. | |
| 5,201,737 A | 4/1993 | Leibinger et al. | |
| 5,300,080 A | 4/1994 | Clayman et al. | |
| 5,330,485 A | 7/1994 | Clayman et al. | |
| 5,464,446 A | 11/1995 | Dreessen et al. | |
| 5,707,373 A | 1/1998 | Sevrain et al. | |
| 5,843,150 A | 12/1998 | Dreessen et al. | |
| 5,865,842 A | 2/1999 | Knuth et al. | |
| 5,927,277 A | 7/1999 | Baudino et al. | |
| 5,954,687 A | 9/1999 | Baudino | |
| 6,006,124 A | 12/1999 | Fischell et al. | |
| 6,044,304 A | 3/2000 | Baudino | |
| 6,050,998 A | 4/2000 | Fletcher | |
| 6,210,417 B1 | 4/2001 | Baudino et al. | |
| 6,321,104 B1 | 11/2001 | Gielen et al. | |
| 6,324,433 B1 | 11/2001 | Errico | |
| 6,482,182 B1 | 11/2002 | Carroll et al. | |

OTHER PUBLICATIONS

Pianca, et al. U.S. Appl. No. 10/052,331, filed Jan. 18, 2002; entitled "Cranial Sealing Plug".

* cited by examiner

*Primary Examiner*—Kevin T Truong
(74) *Attorney, Agent, or Firm*—Vista IP Law Group LLP

(57) ABSTRACT

A cranial burr hole plug with an insertion tool and method of implantation is provided. The burr hole plug includes a shell; a collet interlocked within the shell; a clamp compressing the collet around an elongated medical device exiting the skull of a patient, such as a catheter or lead; and a cover over the clamp, collet, and shell. The insertion tool inserts the collet within the shell and locks the collet around the clamp. The method of implantation includes inserting the burr hole plug components in a cranial burr hole using the insertion tool and securing the exiting medical device without disturbing the position of the medical device.

18 Claims, 8 Drawing Sheets

CRANIAL BURR HOLE PLUG AND INSERTION TOOL

The present application claims the benefit of U.S. Provisional Patent Application Ser. No. 60/403,787, filed Aug. 14, 2002, which application is incorporated herein by reference in its entirety.

FIELD OF THE INVENTION

The present invention relates to methods and apparatuses for securing elongated medical devices such as catheters or leads within a cranial burr hole.

BACKGROUND OF THE INVENTION

Deep brain stimulation (DBS) and other related procedures involving implantation of leads and catheters are increasingly used to treat Parkinson's disease, dystonia, essential tremor, seizure disorders, obesity, depression, restoration of motor control, and other debilitating diseases. During these procedures, a catheter, lead, or other medical device is strategically placed at a target site in the brain. The body of the device then exits through a burr hole cut in the skull. The device must be secured as it exits the skull so as to prevent movement of the device from the precise target site in the brain, and the burr hole must be filled.

Current burr hole plugs placed under the skin of a patient's head are unduly large and unsightly. Further, many current burr hole plugs do not adequately hold the exiting device in place; some force the device to bend at a right angle at the exit without any protection which makes the device vulnerable to fracture or short circuit. During placement of current burr hole plugs, the exiting device often moves from its precise target site in the brain. After placement of current burr hole plugs, the device may migrate over time and will require additional surgical procedures to correct the problem.

Due to a lack of adequate burr hole plugs, many physicians attempt to compensate by securing the device to the skull with sutures and clamping screws, and then filling the burr hole with cyanoacrylate or bone cement. Securing the device with sutures and clamping screws subjects the patient to unnecessary human error. Further, suturing and clamping are cumbersome and time consuming steps. Filling the burr hole with cyanoacrylate or bone cement is messy and permanently locks the device into place, preventing easy access for future necessary procedures.

There is, therefore, a need to provide a relatively small burr hole plug that, without disturbing the position of the device at the target site in the brain, adequately and permanently secures a medical device such as a catheter or lead exiting a burr hole at a gradual angle, but remains accessible for future procedure. Further, there is a need to provide a method of implanting a burr hole plug that mitigates human error and permits safe and efficient implantation.

SUMMARY OF THE INVENTION

The present invention addresses the above and other needs by providing a burr hole plug, a method of implanting the burr hole plug, and an insertion tool. The burr hole plug includes a shell, a collet, a clamp, and a cover. The burr hole plug is smaller than most currently available burr hole plugs. The burr hole plug is installed and secures the exiting device with simultaneous 360° radial pressure from the collet portion of the burr hole plug, thus avoiding disturbance of the position of a medical device at the target site in the brain. The clamp mechanically locks the collet around the body of the medical device without exposing the medical device to pulling, pushing, or twisting forces that could cause unwanted displacement of the medical device from its target site in the brain. The collet simply clamps the medical device from all directions through radial force. The collet, including all other parts of the burr hole plug, is capable of being mechanically unlocked and disassembled to release the medical device and perform any needed future procedures. The device is able to exit the brain at a gradual angle through a conical chamber within the collet, through the tip of the conical chamber where the collet grips the device, and out from underneath the protective cover placed over the collet and clamp.

The method of implantation includes inserting the shell that is sized to friction fit against the inner circumference of the burr hole; interlocking a collet within the shell; placing a clamp over the collet, which clamp compresses the collet as the clamp rotates and interlocks with the shell; and placing a cover over the clamp, collet, and shell. Certain portions of the burr hole plug may be inserted separately or simultaneously using an insertion tool tailored to maximize the efficiency of implantation.

This summary should not be taken in a limiting sense; the scope of the invention should be determined with reference to the claims.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description includes the best mode presently contemplated for carrying out the invention. This description is not to be taken in a limiting sense, but is made merely for the purpose of describing the general principles of the invention. The scope of the invention should be determined with reference to the claims.

The present invention is a burr hole plug, an insertion tool, and a method for implanting the burr hole plug.

Figure 1:
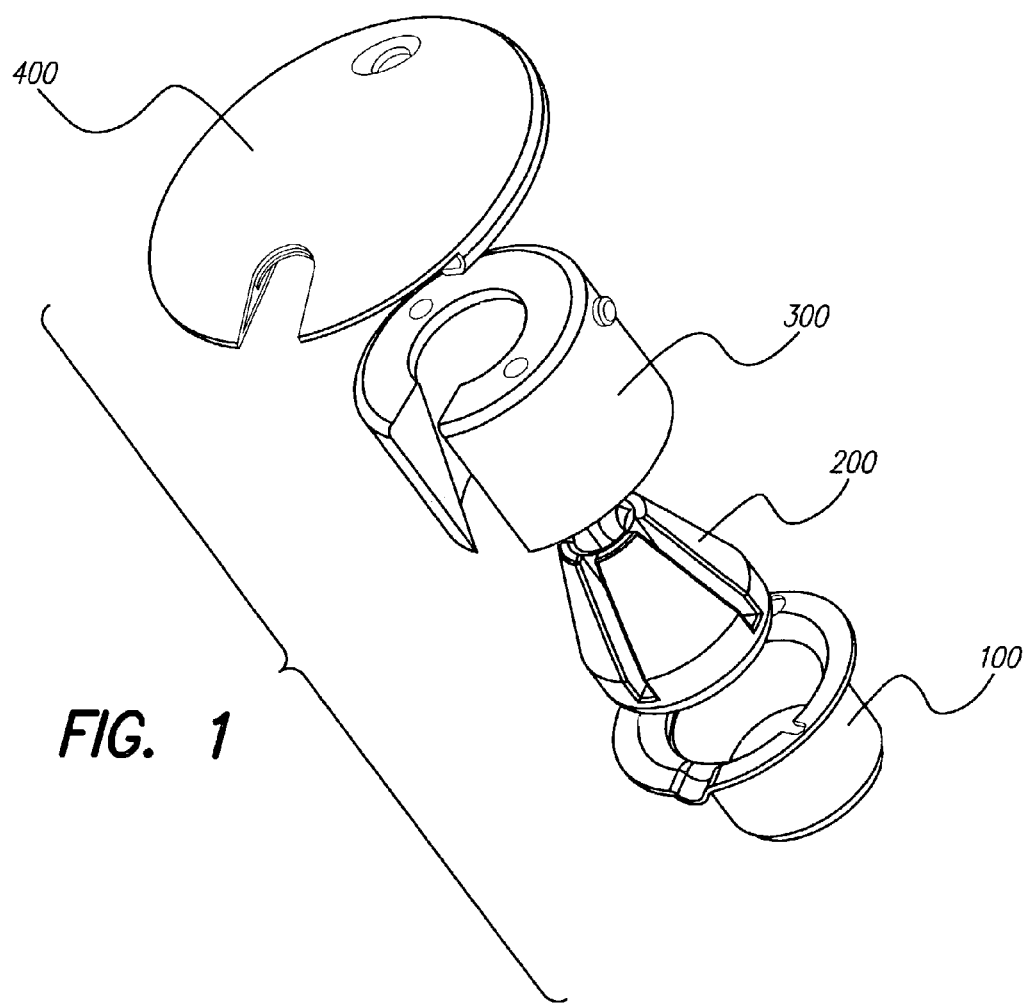
FIG. 1 shows an exploded view of a burr hole plug.

As shown in FIG. 1, the burr hole plug has four main components: a shell 100, a collet 200, a clamp 300, and a cover 400. The burr hole plug, and its components, can be modified to match any shape or size of burr hole in the skull.

Figure 2:
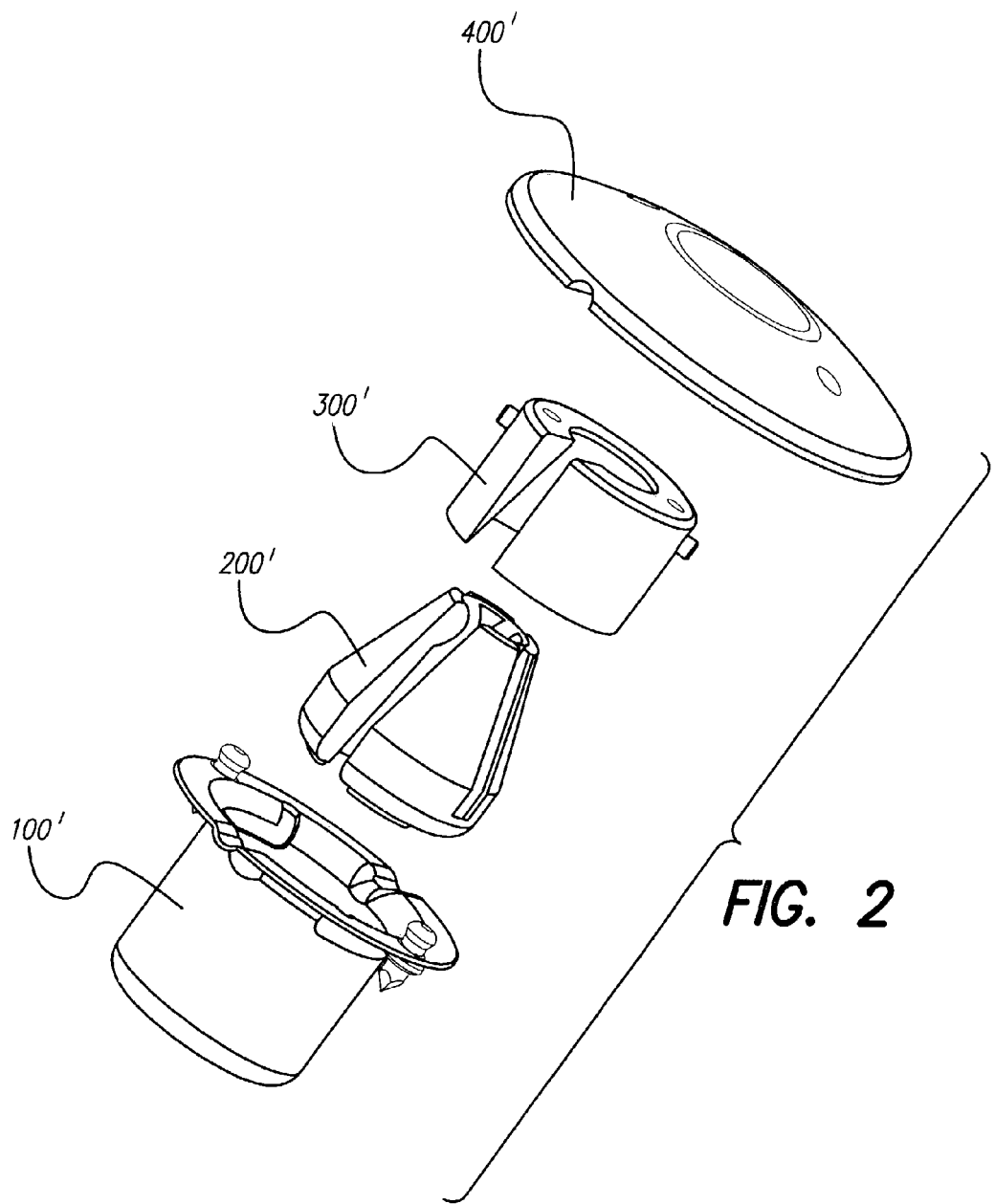
FIG. 2 shows an exploded view of an alternate embodiment of a burr hole plug.

FIG. 2 shows an alternate embodiment of the burr hole plug with four alternate main components: a shell 100', a collet 200', a clamp 300', and a cover 400'. Shell 100' and cover 400' and their various alternate embodiments may be used with collet 200 and clamp 300 of FIG. 1 and their various alternate embodiments to form a number of alternate burr hole plug combinations. Similarly, shell 100 and cover 400 of FIG. 1 and their various alternate embodiments may be used with collet 200' and clamp 300' and their various embodiments to form a number of alternate burr hole plug combinations.

Figure 3:
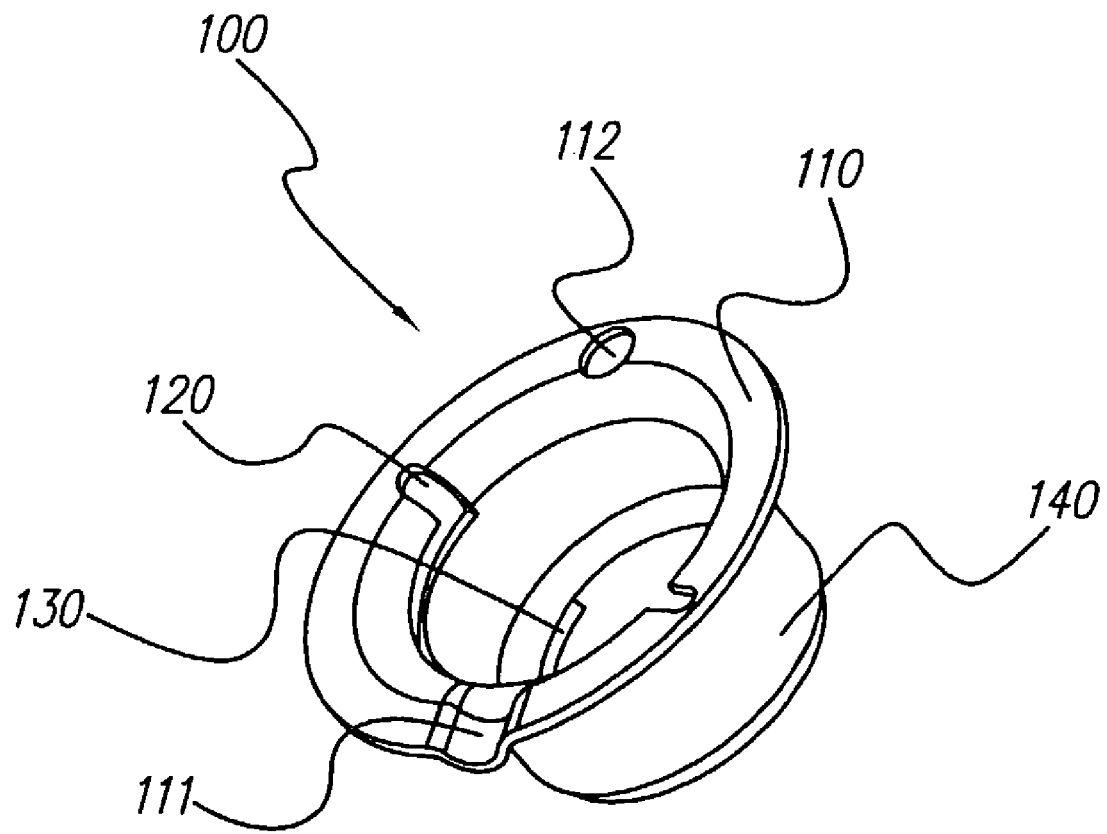
FIG. 3 shows an isometric top view of a shell.

As shown in FIG. 3, shell 100 forms the main part of the burr hole plug of FIG. 1 and is made from any hard biocompatible material such as titanium, stainless steel, other metals or alloys, or hard polymers. Shell 100 includes a flange 110, at least two interlocking slots 120, a locking base 130, and a body 140. An alternate embodiment of shell 100 has a side slot along the full length of shell 100. This permits the alternate embodiment of shell 100 to be inserted into a burr hole after a medical device is inserted into the brain by sliding the body of the medical device through the side slot as the alternate shell 100 is moved into place.

Flange 110 prevents shell 100 from being inserted deeper than the exterior surface of the skull. Flange 110 has a medical device exit 111 that secures the medical device and permits the medical device to gracefully exit the burr hole plug. Alternate embodiments of a medical device exit may include a similar structure such as a channel, hole, bump, tunnel, tube, or gate that secures the medical device and permits the medical device to exit.

Shell 100 is either anchored to the skull, anchored to the skull and cover 400 of FIG. 1, or anchored to cover 400 of FIG. 1. Illustrative embodiments that enable anchoring follow. To anchor shell 100 to the skull, flange 110 includes at least one hole 112 capable of receiving at least one screw or similar anchoring device such as a fastener, pin, spike, tab, or button. Similarly, flange 110 may include, on its undersurface, anchoring structures such as at least one fastener, pin, spike, tab, or button that sinks into the skull where there is at least one corresponding hole (see FIGS. 4A and 4B). To anchor both cover 400 and shell 100 to the skull, a corresponding hole and anchoring device or a corresponding anchor on the undersurface of cover 400 engages with at least one hole 112 on flange 110. To anchor cover 400 to shell 100, flange 110 and cover 400 include at least one other hole (not shown) or at least one other anchoring arrangement using combinable structures such as at least one additional screw and a corresponding hole, at least one button that snaps into a corresponding hole, or at least one ball (see FIGS. 4A and 4B) that friction fits into a corresponding socket (see FIG. 9).

Interlocking slots 120 permit clamp 300 (FIG. 1) to compress and lock collet 200 (FIG. 1) into shell 100. Other structures capable of performing the same function may be substituted for interlocking slots 120.

Locking base 130 permits collet 200 (FIG. 1) to interlock with shell 100 and avoid rotation. Locking base 130 may include any structure or structures capable of locking collet 200 from rotating within shell 100 such as at least one tab, at least one notch, or at least one gear.

Body 140 fits tightly against the inner surface of the circumference of a burr hole in the skull so as to avoid any movement of the burr hole plug in the burr hole after implantation. Additional fixation means or structures may be added to the exterior surface of body 140 to further prevent movement. These means or structures may include, e.g., a rough sandpaper-like surface, notches, or bumps (not shown). Further, vertical or horizontal ribs or threads (not shown) on the exterior surface of body 140 will help prevent rotation of the burr hole plug in the burr hole or vertical movement of the burr hole plug out of or into the burr hole.

Figure 4A:
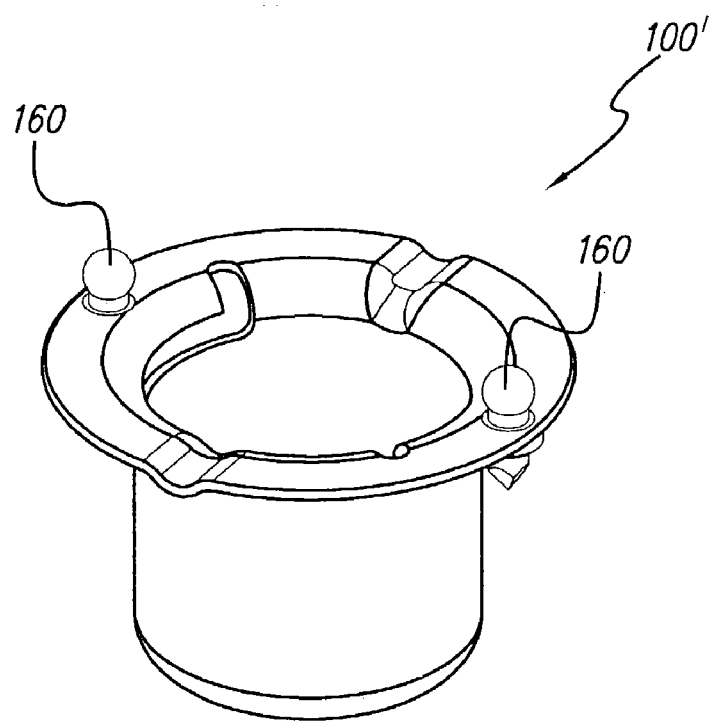
FIG. 4A shows an isometric top front view of an alternate embodiment of a shell.

As shown in FIG. 4A, an alternate embodiment of shell 100' of FIG. 2 employs balls 160 as part of the anchoring arrangement between the shell 100' and cover 400' previously described.

Figure 4B:
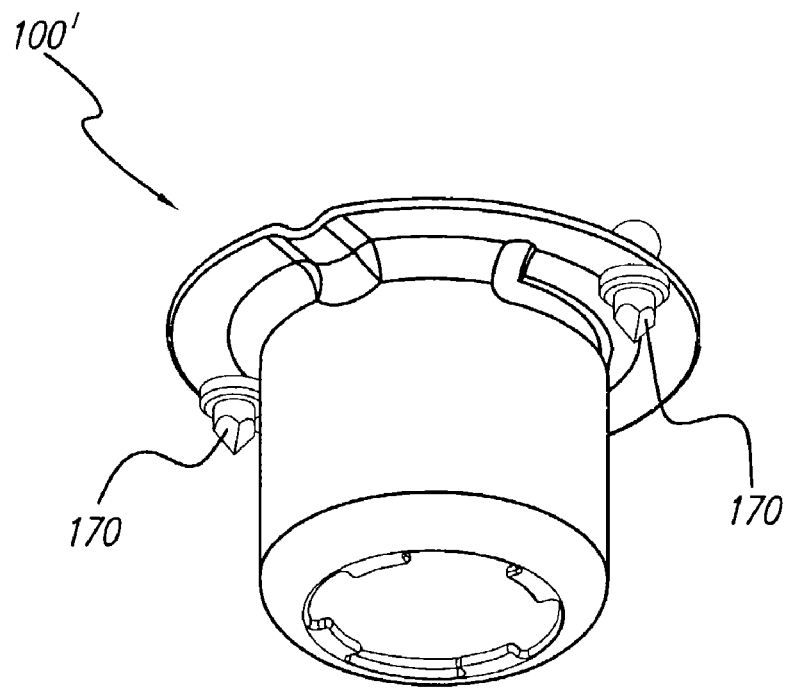
FIG. 4B shows an isometric bottom front view of the shell shown in FIG. 4A.

As shown in FIG. 4B, the shell 100' of FIG. 4A employs pins 170 as structures for anchoring shell 100' to the skull as previously described.

Figure 5A:
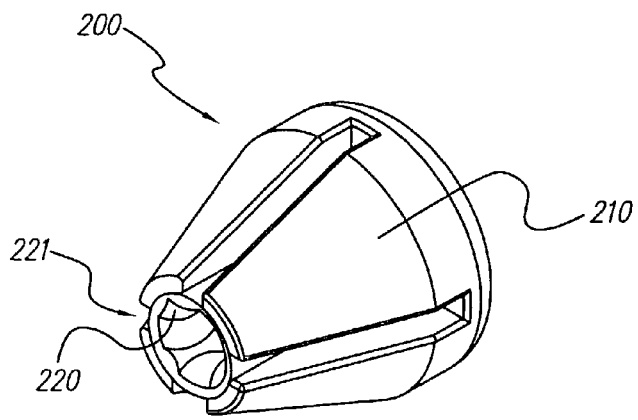
FIG. 5A shows an isometric front view of a collet.

As shown in FIG. 5A, collet 200 of FIG. 1 is made from any hard biocompatible material such as titanium, stainless steel, other metals or alloys, or hard polymers. Collet 200 fits within shell 100 of FIG. 1 and secures a medical device exiting the brain through a burr hole. To secure a medical device, collet 200 includes at least one finger-like gripper 210 and may additionally include at least one cushion 220. FIG. 5A shows four finger-like grippers 210 that, when compressed, centrally secure a medical device using radial force. Alternatively, one "C"-shaped finger-like gripper with a side slot along all or a portion of its length may compress upon itself to centrally secure a medical device using radial force (see FIG. 6). Similarly, one, two, three, five, and any other possible number of finger-like grippers compress upon itself or each other to centrally secure a medical device using radial force. Cushion 220, although not essential to securing a medical device, helps stabilize the medical device within at least one finger-like gripper 210 and helps protect the medical device from damage. At least one cushion 220 is made from a soft biocompatible material such as a soft polymer like silicone rubber or an elastomer. At least one cushion 220 is attached to one or all of finger-like gripper(s) 210 and may be attached at any point on the inside or outside surface of finger-like gripper(s) 210 as long as cushion 220 intermediates finger-like gripper(s) 210 and the medical device at the point of pressure, which is most likely to be at an apex 221 of the collet 200.

Figure 5B:
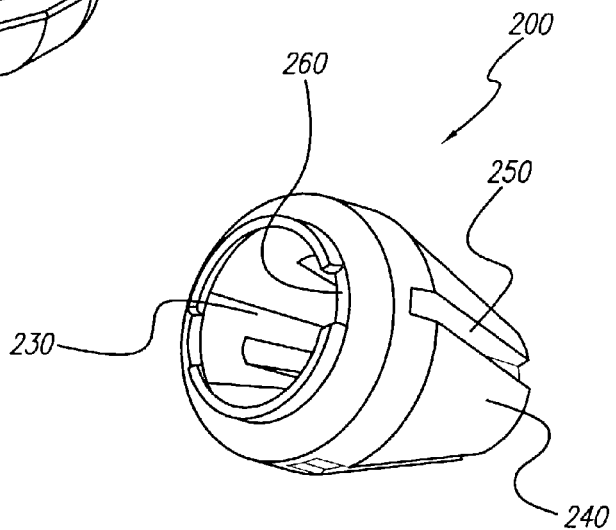
FIG. 5B shows an isometric rear view of the collet shown in FIG. 5A.

As shown in FIG. 5B, collet 200 has an internal conical surface 230 defining an internal conical chamber, an external conical surface 240, at least one side slot 250 along all or a portion of the length of collet 200, and a locking base 260. The internal conical chamber permits a medical device to exit the surface of the brain at any point in the burr hole and subsequently angle toward the apex 221 of the chamber where finger-like gripper(s) 210 secure(s) the medical device. At least one side slot 250 allows at least one finger-like gripper 210 to compress upon itself. Locking base 260 permits collet 200 to interlock with locking base 130 of shell 100 and avoid rotation. Locking base 260 includes any structure or structures capable of interlocking with locking base 130 such as at least one tab, at least one notch, or at least one gear, thus preventing collet 200 from rotating within shell 100.

Figure 6:
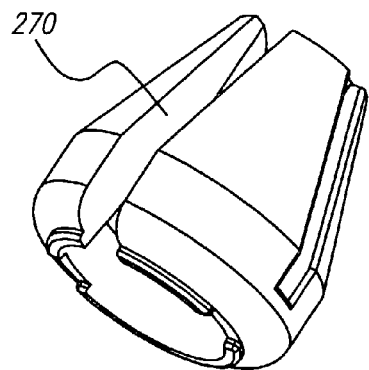
FIG. 6 shows an isometric view of a collet with a side slot.

As shown in FIG. 6, collet 200' of FIG. 2 has a side slot 270 along the full length of collet 200' allowing collet 200' to mount and encircle a medical device at any point along the length of the medical device.

Figure 7:
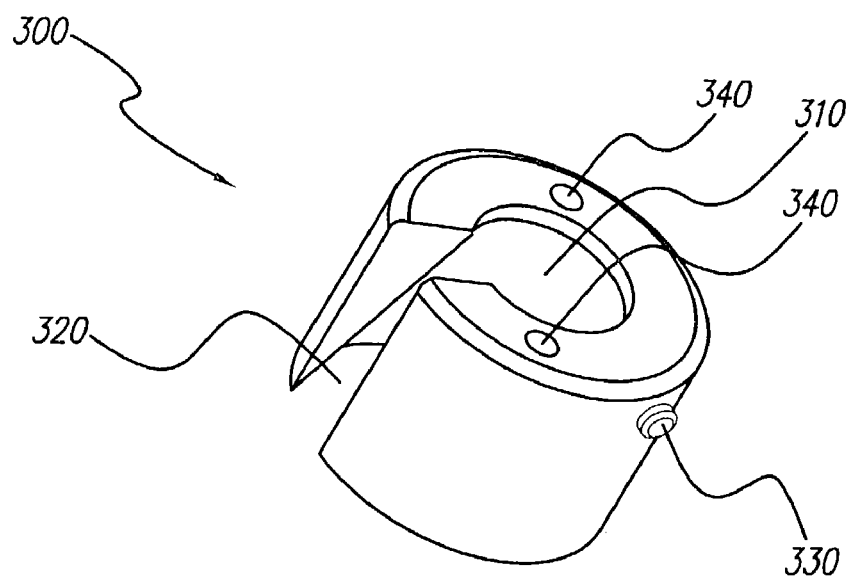
FIG. 7 shows an isometric view of a clamp.
Figure 10:
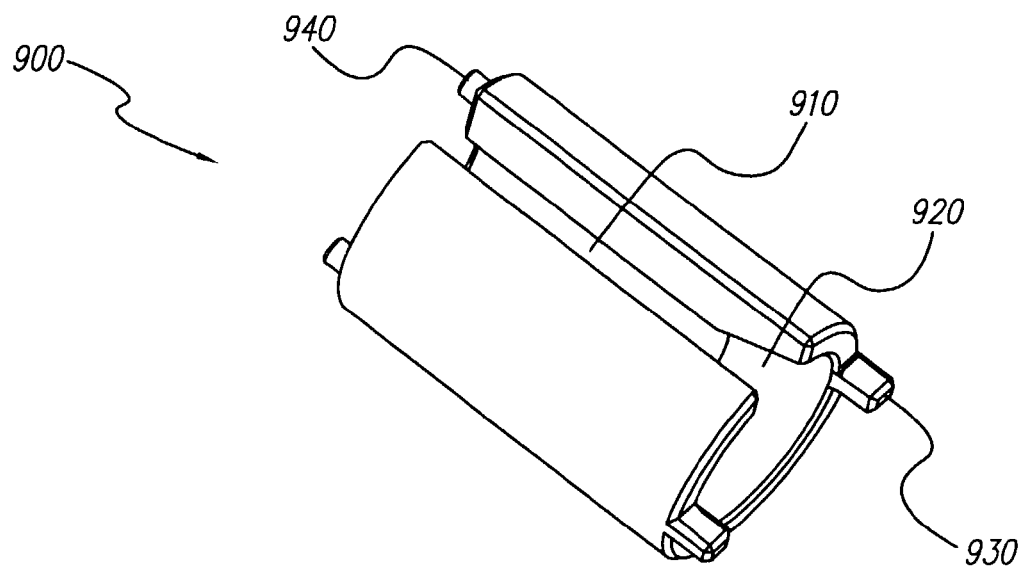
FIG. 10 shows an isometric side view of an insertion tool.

As shown in FIG. 7, clamp 300 of FIG. 1 is made from any hard biocompatible material such as titanium, stainless steel, other metals or alloys, or hard polymers. Clamp 300 locks to shell 100 and compresses finger-like grippers 210 of collet 200. Clamp 300 includes an internal conical surface 310, a side slot 320, at least two pins 330, and holes 340 for engagement with insertion tool 900 (FIG. 10). Internal conical surface 310 engages with external conical surface 240 of collet 200, thereby compressing finger-like grippers 210 as pins 330 are inserted into interlocking slots 120 of shell 100 and clamp 300 is rotatably locked into position on collet 200 and in shell 100. Insertion tool 900 (as shown in FIG. 10) engages holes 340 to apply direction and rotational force to clamp 300 during locking. Any number of holes 340 or similar structures may be used to engage with a corresponding insertion tool. Pins 330 can be any similar structure capable of interlocking with interlocking slots 120 of shell 100 or similar structures. Pins 330 are preferably permanently spaced evenly apart in order to counterbalance each other, i.e., two pins are preferably spaced 180° apart, three pins are preferably spaced 120° apart, and so on.

Figure 8:
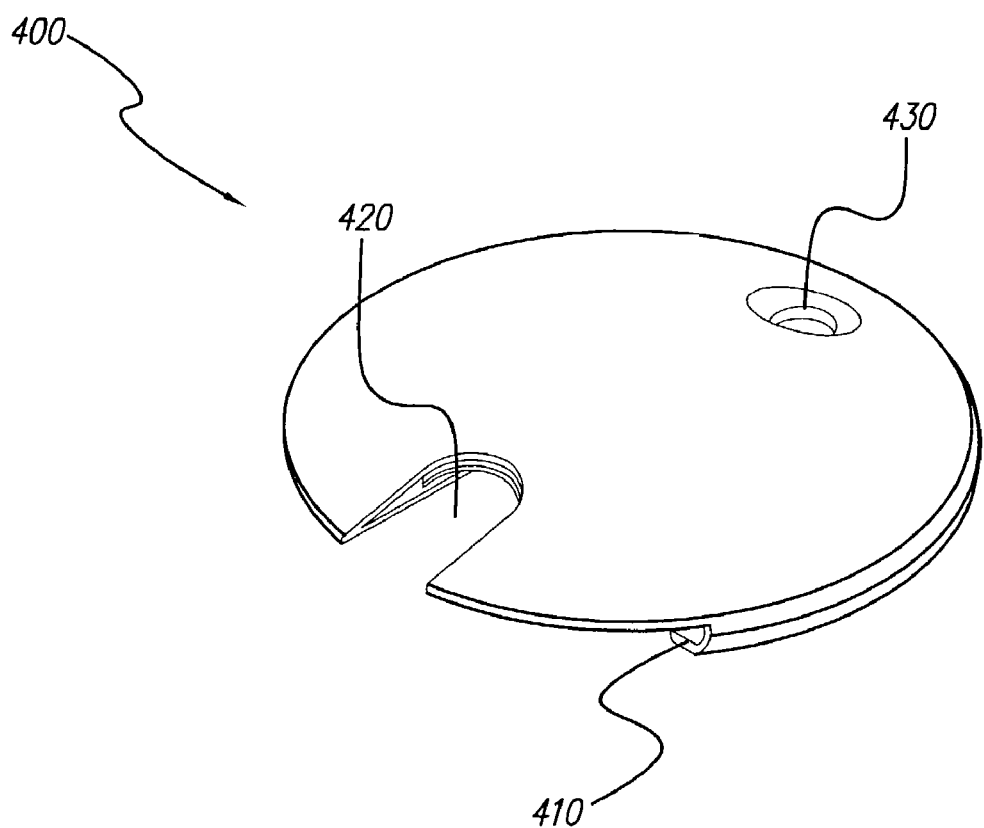
FIG. 8 shows an isometric top view of a cover.

As shown in FIG. 8, plug cover 400 can be made from either a hard or soft biocompatible material such as titanium, another biocompatible metal, a hard polymer, a soft polymer, silastic, an elastomer, or any combination thereof. Cover 400 has an undercut 410 for sliding underneath flange 110 of shell 100. Cover 400 also has a slot 420 for a medical device exit. Alternatively, a channel, hole, bump, tunnel, tube, gate, or similar structure may function as slot 420 to allow a medical device to exit. To anchor both cover 400 and shell 100 to the skull, at least one corresponding hole 430 and anchoring device or a corresponding anchor or other structure on the undersurface of cover 400 engages with at least one hole 112 or other structure on flange 110 of shell 100. To anchor cover 400 to shell 100, flange 110 and cover 400 may have at least one other hole (not shown) or at least one other anchoring arrangement using combinable structures such as at least one additional screw and corresponding hole, at least one button that snaps into a corresponding hole, or at least one ball that friction fits into a corresponding socket.

Figure 9:
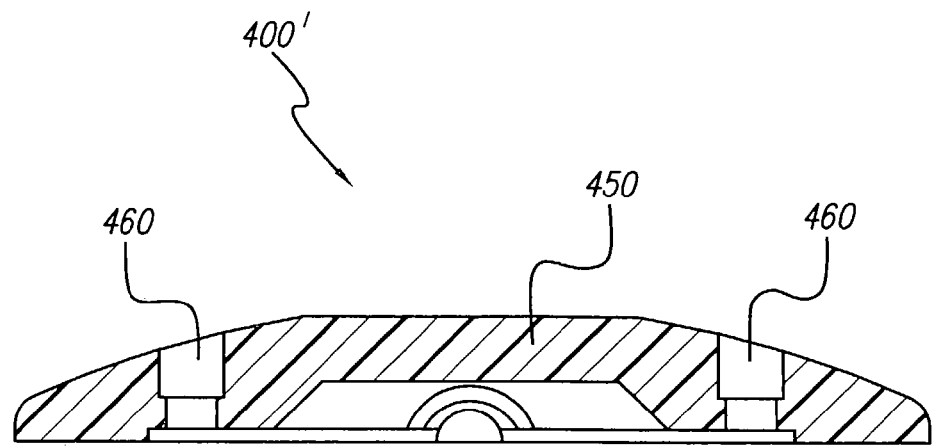
FIG. 9 shows a cross-sectional view of a cover with pin holes.

An alternate embodiment of a cover is shown in FIG. 9 as cover 400' of FIG. 2. Cover 400' is made of a soft biocompatible material 450, such as silastic. Cover 400' has holes 460 for receiving anchors attached to shell 100. An alternate embodiment of a cover (not shown) has an exterior of soft biocompatible material and an interior of hard biocompatible material with anchors attached to the under side of the interior for engagement with the shell and/or skull.

As shown in FIG. 10, an insertion tool 900 is used to implant a burr hole plug. Insertion tool 900 has a side slot 910 along its entire length to permit insertion tool 900 to mount and encircle a medical device at any point along its length. Interior conical surface 920 engages with exterior conical surface 240 to center collet 200 or collet 200', while at least two ribs 930 engage with at least two slots 250 to rotate collet 200 or collet 200' until locking base 260 of collet 200 or collet 200' locks with locking base 130 of shell 100 or shell 100'. At least two pins 940 permit insertion tool 900 to engage with at least two holes 340 and lock clamp 300 or clamp 300' into place by rotating insertion tool 900 and clamp 300 or clamp 300' simultaneously. Ribs 930 and pins 940 are either on opposite ends of the same insertion tool 900 or are on separate tools. The body of insertion tool 900 need not be cylindrical, but can be take any size, shape, or form as long as it is constructed of a hard material such as stainless steel and has structures such as ribs 930 or pins 940 that are compatible with and capable of being engaged with collet 200, collet 200', clamp 300, or clamp 300'.

A method for implanting a burr hole plug includes a combination of the following steps in various orders so that the burr hole plug securely fastens and protects a medical device exiting the skull. Except when necessary, only the structures of the burr hole plug of FIG. 1 are described in the following method. However, this method also applies to the structures of the burr hole plug of FIG. 2 and all other embodiments of the present invention.

A burr hole is created. Shell 100, which is shaped and sized to form a dimensionally close press fit with the internal circumference or surface of the burr hole, is positioned and inserted by being pressed into the hole. If desired, shell 100 is fixed or anchored to the skull by small screws or other anchoring structures. The target site of the medical device in the brain is located, and the medical device is placed in the brain. To close the burr hole plug, collet 200 is carefully inserted into the opening of shell 100 and properly rotated using insertion tool 900 to an interlocking position with shell 100. Clamp 300 is then carefully placed in shell 100 on collet 200 such that pins 330 align with interlocking slots 120 and clamp 300 is pressed and rotated using insertion tool 900 to an interlocking position with shell 100. Compression and rotation of clamp 300 lock clamp 300 into shell 100 and restrain the medical device from further movement in the burr hole.

During the process of closing the burr hole plug, the medical device is not exposed to pulling, pushing, or twisting forces that could cause an unwanted displacement of the medical device from its target site in the brain. The medical device is simply clamped from all directions through radial force from the collet. Plug cover 400 is placed on the top of the burr hole and attached securely by sliding undercut 410 under shell flange 110, employing at least one anchoring arrangement described above.

Alternately, plug cover 400' is anchored to shell 100' and/or the skull using at least one anchoring arrangement described above. Cover 400 or cover 400' protects the medical device at the exit and prevents the medical device from fracturing.

Figure 11:
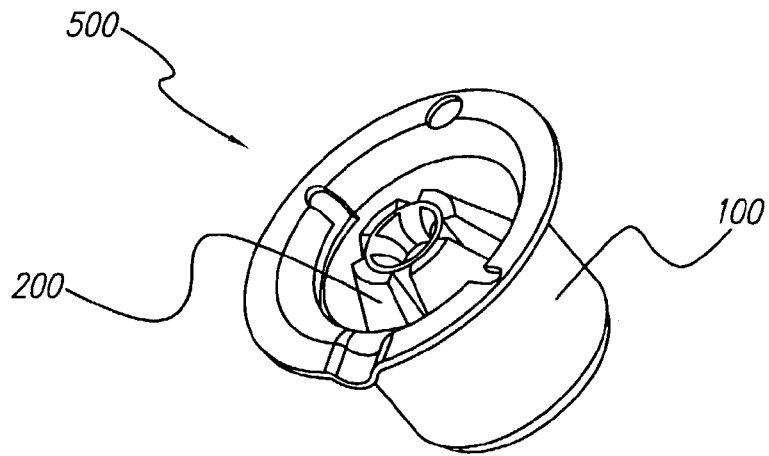
FIG. 11 shows an isometric top view of an integrated shell-collet.

As shown in FIG. 11, shell 100 and collet 200, or their corresponding alternate embodiments, are integrated either permanently, such as by a weld or combined mold, or temporarily, such as by adhesive with a weak bond, to form a shell-collet 500. Integrated shell-collet 500 reduces the number of components for installation thereby reducing the number of steps needed in the insertion and closing procedure. The procedure of inserting a burr hole plug with an integrated shell-collet 500 is essentially the same as the procedure of inserting a burr hole plug with a separate shell 100 and collet 200 except that shell-collet 500 is inserted into the burr hole after the medical device is inserted into the brain. Integrated shell-collet 500 may have a side slot along its full length in order to permit shell-collet 500 to mount and encircle a medical device at any point along the medical device's length.

Figure 12:
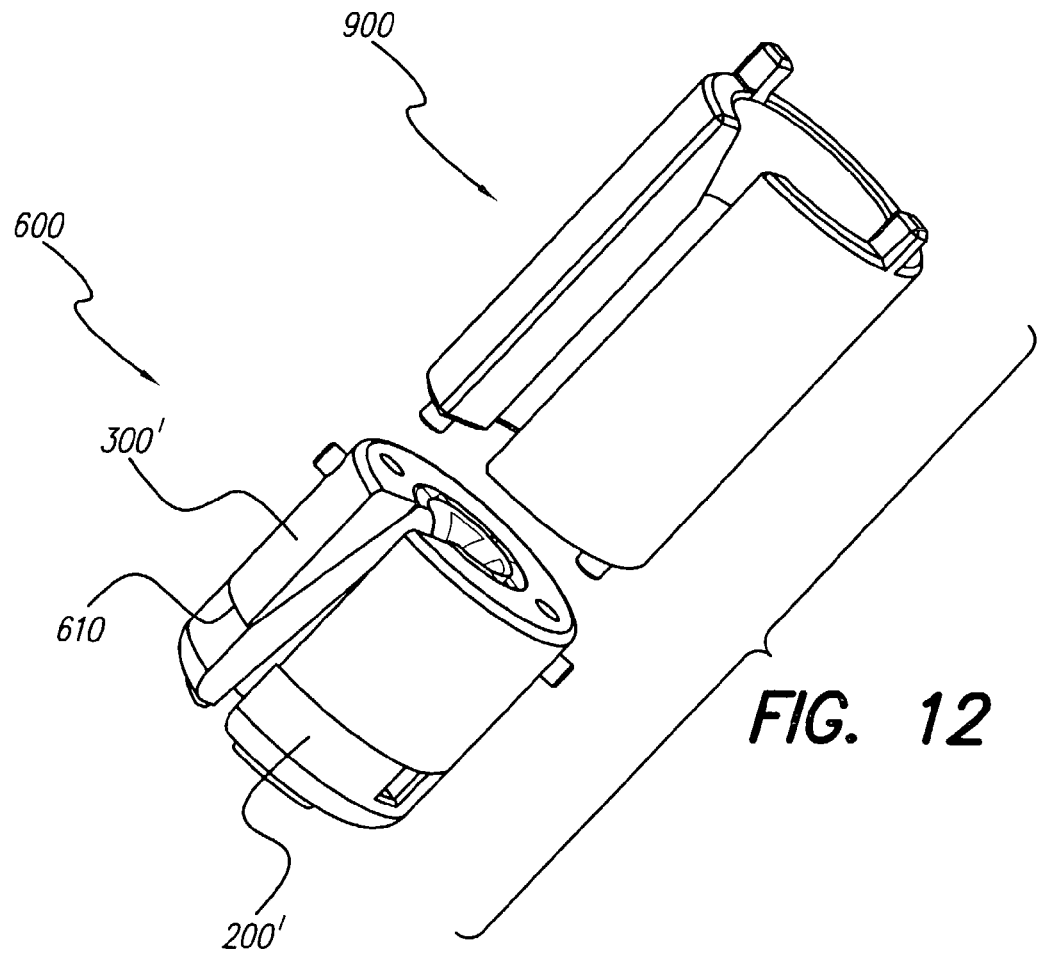
FIG. 12 shows an exploded view of the insertion tool with an integrated collet-clamp for insertion.

As shown in FIG. 12, collet 200' and clamp 300' may be temporarily combined or integrated as by a weak adhesive bond 610 to form collet-clamp 600. Integrated collet-clamp 600 reduces the number of components individually inserted by insertion tool 900 and thus reduces the number of steps needed during a burr hole closing procedure. When insertion tool 900 places collet-clamp 600 into shell 100, locking base 260 of the collet portion of collet-clamp 600 is interlocked with locking base 130 of shell 100, insertion tool and the clamp portion of collet-clamp 600 are rotated, and weak adhesive bond 610 between the collet and clamp portions is broken. When bond 610 is broken, individual collet 200' remains in a locked position in shell 100' or shell 100 and clamp 300' is then rotatably locked against shell 100' or shell 100 by engaging pins 330 of clamp 300' with interlocking slots of shell 100' or interlocking slots 120 of shell 100. Similar weak adhesive, cohesive, magnetized, or other bonds placed prior to procedure may combine various components of the burr hole plug, i.e., shell 100', collet 200', clamp 300', or cover 400', with insertion tools for ease of use and implantation. After the components are placed in locked position, the bond will easily break, allowing an insertion tool to be removed.

While the invention herein disclosed has been described by means of specific embodiments and applications thereof, numerous modifications and variations could be made thereto by those skilled in the art without departing from the scope of the invention set forth in the claims.

What is claimed is:

1. A burr hole plug, comprising:
   a shell capable of being inserted in a burr hole of a skull;
   a collet capable of interlocking with the shell and securing a medical device within the shell when the collet is compressed;
   a clamp capable of interlocking with the shell and compressing the collet; and
   a cover capable of covering the shell, collet, and clamp.

2. The plug of claim 1, wherein the shell further comprises a body and a flange along a top opening of the shell body and wherein the body of the shell defines a side slot along the full length of the body of the shell.

3. The plug of claim 2, wherein the body of the shell includes an exterior surface with a fixation means.

4. The plug of claim 2, wherein the flange includes a medical device exit.

5. The plug of claim 2, wherein the flange includes an anchor for attaching the shell to the skull.

6. The plug of claim 1, wherein the clamp includes a side slot along the full length of the clamp.

7. The plug of claim 1, wherein the collet includes a side slot along the full length of the collet.

8. The plug of claim 1, wherein the cover further comprises an anchor to attach the cover to the skull.

9. The plug of claim 1, wherein the cover and flange of the shell are attached to each other using an anchoring arrangement, wherein the anchoring arrangement is selected from the group consisting of at least one screw and corresponding hole, at least one button that snaps into a corresponding hole, or at least one ball that friction fits into a corresponding socket.

10. The plug of claim 1, wherein the collet includes an apex and wherein at least one compressible soft cushion is attached to the collet at the apex of the collet.

11. The plug of claim 1, wherein the collet includes a body including an internal conical shape.

12. The plug of claim 1, wherein the collet includes a body including an external conical shape.

13. The plug of claim 12, wherein the clamp includes a body including an internal conical shape that is adapted to engage with the external conical shape of the body of the collet.

14. The plug of claim 1, wherein the shell includes at least two interlocking slots and the clamp includes a body that includes at least two externally protruding pins, which pins are adapted to engage with the interlocking slots of the shell.

15. The plug of claim 1, wherein the shell includes a body with a locking base and the collet includes a body with a locking base adapted to interlock with the locking base of the shell.

16. The plug of claim 1, wherein the collet includes at least one slot adapted to engage with an insertion tool and wherein the clamp includes at least one hole adapted to engage with an insertion tool.

17. The plug of claim 1, wherein the shell and the collet are integrated to form a shell-collet.

18. The plug of claim 1, wherein the collet and the clamp are integrated to form a collet-clamp.

* * * * *